US006514537B1

(12) United States Patent
Murphy

(10) Patent No.: US 6,514,537 B1
(45) Date of Patent: Feb. 4, 2003

(54) MAGNESIUM CITRATE SOLUTION

(75) Inventor: William R. Murphy, Murfreesboro, TN (US)

(73) Assignee: Cumberland Swan Holdings, Inc., Smyrna, TN (US)

(*) Notice: Subject to any disclaimer, the term of this patent is extended or adjusted under 35 U.S.C. 154(b) by 0 days.

(21) Appl. No.: 09/867,017

(22) Filed: May 29, 2001

Related U.S. Application Data

(60) Provisional application No. 60/208,818, filed on Jun. 2, 2000.

(51) Int. Cl.$^7$ ............................................. A61K 33/08
(52) U.S. Cl. ...................... 424/692; 514/892; 514/574
(58) Field of Search ..................... 424/692; 514/892, 514/574

(56) References Cited

U.S. PATENT DOCUMENTS

| | | |
|---|---|---|
| 2,363,108 A | 11/1944 | Kane et al. |
| 3,211,614 A | 10/1965 | Embring et al. |
| 4,468,381 A * | 8/1984 | Mitra et al. ................ 424/158 |
| 4,664,920 A | 5/1987 | Saleeb et al. |
| 4,716,153 A | 12/1987 | Morishita et al. |
| 5,213,838 A | 5/1993 | Sheikh |
| 5,219,889 A | 6/1993 | Walsdorf et al. |
| 5,432,200 A | 7/1995 | Walsdorf et al. |
| 5,780,046 A | 7/1998 | Humber et al. |
| 5,811,131 A | 9/1998 | Mackles et al. |
| 5,858,403 A | 1/1999 | Borody et al. |
| 5,958,445 A | 9/1999 | Humber et al. |

OTHER PUBLICATIONS

Goodman & Gilmna's The Pharmacological Basis of Therapeutics, Ninth Edition, (1996), p. 921.*
United States Pharmacopoeia, United States Pharmacopeial Convention, Inc., Rockville Maryland. USP 24, p. 1003. (2000).
Journal of the American Pharmaceutical Association, vol. XXV, pp. 1108–1112, (1936).
The Dispensatory of the United States of America (23rd Edition), Part 1, pp. 631–623, (1943).
The Dispensatory of the United States of America (25th Edition), Part 1, pp. 774–775, (1955).
Remington's Practice of Pharmacy, Cook et al., pp. 554–555, (1951).

* cited by examiner

Primary Examiner—Dwayne C. Jones
Assistant Examiner—C. Delacroix-Muirheid
(74) Attorney, Agent, or Firm—Waddey & Patterson, P.C.; Douglas W. Schelling

(57) ABSTRACT

A magnesium citrate oral solution comprising citric acid in an amount greater than 10% weight/volume; magnesium hydroxide in an amount ranging from about 1.5–5% weight/volume; and water. Most preferably, the citric acid is present in an amount of about 10.9% weight/volume. Another embodiment of the present invention is a method of treating constipation in a patient in need thereof. The method of this embodiment comprises administering an effective amount of an oral composition that comprises citric acid in an amount greater than 10% weight/volume. Preferably, the composition of this embodiment comprises citric acid in an amount of 10.9% weight/volume.

19 Claims, No Drawings

MAGNESIUM CITRATE SOLUTION

PRIORITY

This application claims priority under 35 U.S.C. §120 to Application No. 60/208,818 filed Jun. 2, 2000, the contents of which are incorporated herein by reference.

FIELD OF THE INVENTION

The present invention relates to a novel magnesium citrate solution.

BACKGROUND OF THE INVENTION/ Description of the Prior Art

The therapeutic use of magnesium citrate as a gentle laxative is well known. Magnesium citrate oral solutions are considered saline laxatives that are widely available over the counter. Magnesium citrate attracts and retains water in the intestine, softening stools and inducing the urge to defecate. A typical dose for adults is about 10 to 14 ounces daily in 1 or more doses.

Relevant background information and prior art oral solutions are discussed below.

U.S. Pat. No. 2,363,108 to Kane et al., issued on Nov. 21, 1944, incorporated herein by reference, describes a stable laxative composition comprising magnesium fumarate, fumaric acid and sodium bicarbonate. See Example 3, which describes the solution as having similar properties as magnesium citrate.

U.S. Pat. No. 4,664,920 to Saleeb et al., issued on May 12, 1987, incorporated herein by reference, discloses a method for fixing a water-soluble water-dispersible or water-emulsifiable food ingredient that comprises magnesium salts of citric acid. See examples 5 and 6 where aqueous magnesium citrate solutions were prepared.

U.S. Pat. No. 5,219,889 to Walsdorf et al., issued on Jun. 15, 1993, incorporated herein by reference, describes a potassium magnesium citrate used as dietary supplement.

U.S. Pat. No. 5,432,200 to Walsdorf et al., issued on Jul. 11, 1995, incorporated herein by reference, is a division of U.S. Pat. No. 5,219,889.

U.S. Pat. No. 5,780,046 to Humber et al., issued on Jul. 14, 1998, incorporated herein by reference, describes an oral formulation of ibuprofen comprising citric acid, sodium benzoate and disodium edetate. See Examples 1 and 2.

U.S. Pat. No. 5,811,131 to Mackles et al., issued on Sep. 22, 1998, incorporated herein by reference, describes a tasteless liquid composition. The loperamide suspension of Example 1 contains magnesium hydroxide and citric acid.

U.S. Pat. No. 5,958,445 to Humber et al., issued on Sep. 28, 1999, incorporated herein by reference, describes an oral formulation comprising citric acid, sodium benzoate and disodium edetate. See Examples 1 and 2.

U.S. Pat. No. 3,211,614 to Embring et al., issued on Oct. 12, 1965, incorporated herein by reference, describes a laxative composition consisting essentially of the following ingredients: an alkali salt of an aliphatic polybasic hydroxy acid such as citric acid; an alcohol; and water.

U.S. Pat. No. 4,716,153 to Morishita et al., issued on Dec. 29, 1987, incorporated herein by reference, describes citric acid is used as dissolution accelerator to prepare stable oral antibiotic formulation.

U.S. Pat. No. 5,858,403 to Borody et al., issued on Jan. 12, 1999, incorporated herein by reference, describes an osmotic colonic evacuant in solid dosage form comprising a phosphate/sulfate based laxative, sodium picosulfate and an antacid, for example, magnesium citrate/magnesium oxide with citric acid. See col. 6 table and lines 56–58. The patent describes a powder formulation that can be encapsulated. According to the disclosure, the capsules can also be used as a laxative.

U.S. Pat. No. 5,213,838 to Sheikh, issued on May 25, 1993, incorporated herein by reference, describes a sodium-free composition prepared from a solution containing sufficient citric acid to provide an initial solution pH equal to or less than about 3.5. The composition has primary components of potassium citrates, calcium citrates, and mixtures thereof. The composition may additionally contain amounts of magnesium citrate suitable for therapeutic use as a gentle dietary laxative. The solutions of this disclosure are added to citric acid in an amount to raise the pH to about 3.5. See example 1 and claim 1.

SUMMARY OF THE INVENTION

The present invention relates to a magnesium citrate formulation that has an increased citric acid level. In another embodiment of the present invention, the magnesium citrate oral solution has an increased citric acid level and the incorporation of a suitable preservative.

As stated above, the therapeutic use of magnesium citrate as a gentle laxative is well known. The inventor has developed an improved magnesium citrate solution that has a lower crystallization level, does not require pasteurization, requires less filtering during production, and is less expensive to produce. Furthermore, the magnesium citrate solution of the present invention is less susceptible to microbial contamination and has a longer shelf live than traditional magnesium citrate solutions.

As discussed above, the novel magnesium citrate solution of the present invention has a therapeutic use as a gentle laxative and has many benefits over traditional oral magnesium citrate solutions.

One embodiment of the present invention, a magnesium citrate oral solution comprises citric acid in an amount greater than 10% weight/volume; magnesium hydroxide in an amount ranging from about 1.5–5% weight/volume; and water. Most preferably, the citric acid is present in an amount of about 10.9% weight/volume. Additionally, preferably the magnesium hydroxide is present in an amount of from 1.5 to 3.0% weight/volume. More preferably, the magnesium hydroxide is present in an amount of from 2.0 to 3.0% weight/volume.

Another embodiment of the present invention is a method of treating constipation in a patient in need thereof. The method of this embodiment comprises administering an effective amount of an oral composition that comprises citric acid in an amount greater than 10% weight/volume. Preferably, the composition of this embodiment comprises citric acid in an amount of 10.9% weight/volume.

DETAILED DESCRIPTION OF THE INVENTION

The magnesium citrate solution of the present invention comprises a citric acid level of over 10% w/v. The present inventor has found that increasing the citric acid level, among other things, eliminates the propensity of the active ingredient of the solution to crystallize in the bottle upon aging. Additionally, the magnesium citrate solution of the present invention is less susceptible to microbial contamination. For example, *Staph. hominis* and *Bacillus coagulans* organisms have been recovered from commercial magnesium citrate solutions. The present invention is much less susceptible to such contamination.

Current United States Pharmacopoeia standards do not specify a maximum level for citric acid. The USP standard only sets forth a minimum of 7.59% weight/volume. The current industry practice is approximately 8.95% weight/volume.

Additionally, the current practice with respect to magnesium citrate solutions is to require a pasteurization step. This is because a non-pasteurized solution may crystallize in a very short period of time. In some instances, crystallization will occur in two months or less. The present inventor has discovered a formula for an oral solution that will not crystallize in the absence of a pasteurization step.

In one embodiment of the present invention, benzoic acid is added as a preservative. The addition of preservatives is preferred because, even though typically directed to, in many cases consumers do not ingest an entire bottle in a single dose. That is, even though magnesium citrate solutions are typically packaged as single dose units, they are many times only partially ingested and the remaining product is saved for a later application. The incidence of microbial contamination (including mold and yeast contamination) is greater in the remaining portion of the unpreserved product than with a preserved product. Pasteurization reduces the microbial load in the product, but does not prevent microbes from being introduced after the bottle is opened. Unfortunately, a typical magnesium citrate formula provides microbes with an ideal environment to grow and flourish. However, these embodiments of the present invention provide a continual defense against the growth of microbes in a partially used unit.

Additionally, the uniqueness of these embodiments allows for the use of plastic bottles instead of glass. The primary reason that these embodiments permit the use of plastic bottles (as opposed to the traditional glass) is that the magnesium citrate solution is not carbonated. With many commonly available plastic bottles the pressure from carbonation could create problems with the shelf life of the product and could deform the plastic bottle. Additionally, the carbonated formula in many plastic bottles may allow the carbonation to dissipate fairly rapidly, thus changing the aesthetics of the formula. However, using plastic in the manufacturing process allows for a lower manufacturing cost which in many instances may be passed on to the consumer.

As stated above, one embodiment of the present invention is a magnesium citrate oral solution that comprises citric acid in an amount greater than 10% weight/volume; magnesium hydroxide in an amount ranging from about 1.5–5% weight/volume; and water. Preferably, the citric acid is present in an amount of about 10.5–20% weight/volume. More preferably, the citric acid is present in an amount of about 10.5–15% weight/volume. Most preferably, the citric acid is present in an amount of about 10.9% weight/volume.

In another embodiment of the present invention, magnesium hydroxide is present in an amount of from about 2–3% weight/volume.

In other embodiments of the present invention, the oral solution may contain benzoic acid. Preferably, the benzoic acid is present in an amount of from 0.01–0.1% weight/volume. More preferably, the benzoic acid is present in an amount of from 0.025–0.075% weight/volume. More preferably, the benzoic acid is present in an amount from 0.04 to 0.06% weight/volume. The benzoic acid in the oral solution of the present invention functions as a preservative.

In other embodiments of the present invention, the oral solution may contain sodium saccharin. The sodium saccharin may be adjusted as necessary to achieve the desired taste. Preferably, the sodium saccharin is present in an amount of about 0.070% weight/volume. The sodium saccharin in the oral solution of the present invention functions as a sweetener.

In other embodiments of the present invention, the oral solution may contain disodium EDTA. Preferably, the disodium EDTA is present in an effective chelating amount such as about 0.02% weight/volume. The disodium EDTA in the oral solution of the present invention functions as a chelating agent and therefore may be added to the solution to chelate small amounts of metals that may be present in the raw materials.

The oral solution of the present invention may comprise at least one of a flavoring additive or a dye. The exact nature of the flavoring additive or dye is not known to be critical, as long as the flavoring additive or dye does not interfere with the efficacy or function of the oral solution. One of ordinary skill in the art can select and employ desired flavoring additives or dyes as well as the proper amounts to use so as to not interfere with the desired function of the oral solution of the present invention. For example, the solution of the present invention may comprise any flavoring additive or dye commonly used in the industry. For example, the solution of the present invention may comprise lemon oil, cherry flavor and/or dyes such as FD&C Red #40.

In a preferred embodiment of the present invention, the oral solution comprises citric acid, present in an amount of about 10.5–15% weight/volume; magnesium hydroxide, present in an amount ranging from about 2–3% weight/volume; and the oral solution further comprises benzoic acid; sodium saccharin; and disodium EDTA.

As stated above, the present invention also comprises a method of treating constipation in a patient in need thereof. The method of this embodiment comprises administering an effective amount of an oral solution as described herein, comprising citric acid in an amount greater than 10% weight/volume. That is, preferably the composition of this embodiment comprises citric acid in an amount of 10.5–20% weight/volume; more preferably about 10.9%. Additionally, the composition of this embodiment preferably further comprises magnesium hydroxide in an amount ranging from about 1.5–5% weight/volume. Furthermore, as described above, the composition may further comprise benzoic acid, sodium saccharine, disodium EDTA, flavoring additives, and dyes.

In the method if the present invention, the administration step further comprises administering about 100 ml–400 ml orally. The dosage may change depending on the need of the user and one of ordinary skill in the art can make such changes. In one embodiment of the present invention, the dose of the oral composition is the same as the doses for prior art magnesium citrate solutions.

The oral solution of the present invention may be made in a similar fashion as prior art magnesium citrate solutions. For example, the techniques for making the solution of the present invention are similar to those described for magnesium citrate solutions in the United States Pharmacopeia, incorporated herein by reference; Remington's Practice of Pharmacy, incorporated herein by reference; and the Dispensatory of the United States of America, incorporated herein by reference.

Other features of the invention will become apparent in the course of the following examples which are given for illustration of the invention and are not intended to be limiting thereof.

EXAMPLE 1

The following is an example of a magnesium citrate formula of the present invention:

| Item | Kg/Liter | g/batch |
| --- | --- | --- |
| Purified Water, USP | 0.92609 | 6920 g |
| Citric Acid, USP | 0.10900 | 740 g |
| Magnesium Hydroxide, USP | 0.02370 | 161 g |
| Benzoic Acid, USP | 0.00050 | 3.40 g |
| Sodium Saccharin, USP | 0.00070 | 4.75 g |
| Disodium EDTA, USP | 0.00020 | 1.36 g |
| Lemon oil | 0.00600 g | 0.04 g |

The water is added to a 10 liter plastic beaker. The water is mixed after the citric acid is added and is mixed 10 minutes after addition is complete. The magnesium hydroxide is added and the solution is mixed for 10 minutes. The benzoic acid, disodium EDTA, sodium saccharin, and the lemon oil are added. The solution is mixed for one hour. In this small batch example, after mixing the solution is filtered through a Wattman #4 filter into individual bottles. For larger batches, a suitable filter and filtration technique may be chosen. The total batch size for this example is 6792 ml.

EXAMPLE 2

The following is an example of a magnesium citrate formula of the present invention:

| Item | kg/liter | g/Batch |
| --- | --- | --- |
| Purified water, USP | 0.925648 | 6287 |
| Citric acid, USP | 0.10900 | 740 |
| Magnesium Hydroxide, USP | 0.02370 | 161 |
| Benzoic Acid, USP | 0.00050 | 3.40 |
| Sodium Saccharin, USP | 0.00070 | 4.75 |
| Disodium EDTA, USP | 0.00020 | 1.36 |
| Cherry Flavor | 0.00014 | 0.95 |
| FD&C #40 (dye), USP | 0.22250 g | 1.51 |

The solution is prepared in the same manner as the solution of Example 1, except that the flavor of this example is used in place of the flavor of Example 1, and the dye is added in the same step the flavor is added. The total batch size is 6792 ml.

EXAMPLE 3

The following is an example of a magnesium citrate oral solution of the present invention:

| Item | kg/l | g/batch |
| --- | --- | --- |
| Purified water, USP | 0.92609 | 7409 |
| Citric acid, USP | 0.10900 | 872 |
| Magnesium Hydroxide, USP | 0.02370 | 190 |

-continued

| Item | kg/l | g/batch |
| --- | --- | --- |
| Benzoic acid, USP | 0.00050 | 400 |
| Sodium Saccharin, USP | 0.00070 | 5.60 |
| Disodium EDTA, USP | 0.00020 | 1.60 |
| Lemon Oil | 0.00600 g | 0.048 |

The solution is prepared in the same manner as the solution of Example 1, except that 0.91 g of $NaHCO_3$ is added to the bottles before capping. The total batch size is 8000 ml.

EXAMPLE 4

The following is an example of a magnesium citrate oral solution of the present invention:

| Item | Kg/L | g/batch |
| --- | --- | --- |
| Purified water, USP | 0.92609 | 7409 |
| Citric Acid, USP | 0.10900 | 872 |
| Magnesium Hydroxide, USP | 0.02370 | 190 |
| Benzoic Acid, USP | 0.00050 | 4.00 |
| Sodium Saccharin, USP | 0.00070 | 5.60 |
| Disodium EDTA, USP | 0.00020 | 1.60 |
| Lemon Oil | 0.00600 g | 0.048 |

The solution is prepared in the same manner as the solution of Example 3, except that 1.35 g of $NaHCO_3$ is added to the bottles before capping. The total batch size is 8000 ml.

EXAMPLE 5

The following is a comparative example of a magnesium citrate oral solution:

| Item | Kg/L | G/batch |
| --- | --- | --- |
| Purified Water, USP | 0.93559 | 7485 |
| Citric Acid, USP | 0.09950 | 796 |
| Magnesium Hydroxide, USP | 0.02370 | 190 |
| Benzoic Acid, USP | 0.00050 | 4.00 |
| Sodium Saccharin, USP | 0.00070 | 5.60 |
| Disodium EDTA, USP | 0.00020 | 1.60 |
| Lemon Oil | 0.00600 g | 0.048 |

The solution is prepared in the same manner as the solution of Example 3. The total batch size is 8000 ml.

EXAMPLE 6

This comparative example has the same formula as the solution of Example 5, except that 1.05 g of $KHCO_3$ (instead of $NaHCO_3$) is added to each bottle. The total batch size is 8000 ml.

EXAMPLE 7

This Example compares Example 1–6 with respect to crystallization.

| Example | % citric acid | Bicarbonate level | Crystallizes at: |
|---|---|---|---|
| 1 | 10.9 | 0 | None at 3 years |
| 2 | 10.9 | 0 | None at 3 years |
| 3 | 10.9 | 0.5 | 30 months |
| 4 | 10.9 | 0.5 | 30 months |
| 5 | 9.95 | 0.5 | 18 months |
| 6 | 9.95 | 0.5 | 18 months |

All cited patented publications referred to in this application (including all attachments) are herein expressly incorporated by reference.

This invention thus being described, it will be obvious that the same may be varied in many ways. Such variations are not regarded as a departure from the spirit and scope of the present invention, and all such modifications as would be obvious to one of ordinary skill in the art are intended to be included within the scope of this invention and in the following claims.

I claim:

1. A magnesium citrate oral solution, comprising:
   citric acid in an amount greater than 10% weight/volume;
   magnesium hydroxide in an amount ranging from about 1.5–5% weight/volume; and
   water.
2. The oral solution of claim 1, wherein:
   said citric acid is present in an amount of about 10.5–20% weight/volume.
3. The oral solution of claim 1, wherein:
   said citric acid is present in an amount of about 10.5–15% weight/volume.
4. The oral solution of claim 1, wherein:
   said citric acid is present in an amount of about 10.9% weight/volume.
5. The oral solution of claim 1, wherein:
   said magnesium hydroxide is present in an amount of from about 2–3% weight/volume.
6. The oral solution of claim 1, further comprising:
   benzoic acid in an amount of from about 0.025–0.075 weight/volume.
7. The oral solution of claim 1, further comprising:
   sodium saccharin in an amount of about 0.070% weight/volume.
8. The oral solution of claim 1, further comprising:
   at least one of a flavoring additive or a dye.
9. The oral solution of claim 8, wherein:
   the citric acid is present in an amount of about 10.5–15% weight/volume;
   the magnesium hydroxide is present in an amount ranging from about 2–3% weight/volume; and the oral solution further comprises:
   benzoic acid;
   sodium saccharin; and
   disodium EDTA.
10. The oral solution of claim 1, comprising (weight/volume):
    citric acid in an amount of about 10.9%;
    magnesium hydroxide in an amount of about 2.4%;
    benzoic acid in an amount of about 0.05%;
    sodium saccharin in an amount of about 0.07%; and
    disodium EDTA in an amount of about 0.02%.
11. A method of treating constipation in a patient in need thereof, comprising: administering an effective amount of a magnesium citrate oral composition that comprises: citric acid in an amount greater than 10% weight/volume.
12. The method of claim 11, wherein:
    the composition further comprises magnesium hydroxide in an amount ranging from about 1.5–5% weight/volume.
13. The method of claim 11, wherein:
    the composition comprises citric acid in an amount of 10.5–20% weight/volume.
14. The method of claim 11, wherein:
    the composition comprises citric acid in an amount of 10.5–15% weight/volume.
15. The method of claim 11, wherein:
    the composition comprises citric acid in an amount of 10.9% weight/volume.
16. The method of claim 11, wherein:
    the administration step further comprises administering about 100–400 ml orally.
17. The method of claim 11, wherein:
    the composition comprises:
    citric acid is present in an amount of about 10.5–15% weight/volume;
    magnesium hydroxide is present in an amount ranging from about 2–3% weight/volume;
    benzoic acid;
    sodium saccharin; and
    disodium EDTA.
18. The method of claim 11, wherein:
    the composition further comprises at least one of a flavor additive or a coloring dye.
19. The method of claim 11, wherein:
    the composition comprises:
    citric acid in an amount of about 10.9%;
    magnesium hydroxide in an amount of about 2.4%;
    benzoic acid in an amount of about 0.05%;
    sodium saccharin in an amount of about 0.07%; and
    disodium EDTA in an amount of about 0.02%.

* * * * *